(12) United States Patent
Hazra et al.

(10) Patent No.: US 9,090,705 B2
(45) Date of Patent: Jul. 28, 2015

(54) PROCESS FOR PREPARATION OF INSULIN COMPOUNDS

(75) Inventors: Partha Hazra, Karnataka (IN); Srikanth Gollarahosahalli Sathyanarayana, Karnataka (IN); Suma Sreenivas, Karnataka (IN); Manjunath Hadavanahalli Shivarudraiah, Karnataka (IN); Kedarnath Nanjund Sastry, Karnataka (IN); Harish Iyer, Karnataka (IN)

(73) Assignee: Biocon Limited (IN)

( * ) Notice: Subject to any disclaimer, the term of this patent is extended or adjusted under 35 U.S.C. 154(b) by 253 days.

(21) Appl. No.: 13/057,317

(22) PCT Filed: Sep. 19, 2008

(86) PCT No.: PCT/IN2008/000598
§ 371 (c)(1),
(2), (4) Date: Feb. 3, 2011

(87) PCT Pub. No.: WO2010/016069
PCT Pub. Date: Feb. 11, 2010

(65) Prior Publication Data
US 2011/0159538 A1    Jun. 30, 2011

(30) Foreign Application Priority Data
Aug. 7, 2008  (IN) .......................... 01904/CHE/2008

(51) Int. Cl.
| C12P 21/06 | (2006.01) |
| A61K 38/28 | (2006.01) |
| C07K 14/62 | (2006.01) |
| A61K 38/00 | (2006.01) |
| A61P 3/08  | (2006.01) |
| A61P 3/10  | (2006.01) |

(52) U.S. Cl.
CPC C07K 14/62 (2013.01); C12P 21/06 (2013.01)

(58) Field of Classification Search
None
See application file for complete search history.

(56) References Cited

U.S. PATENT DOCUMENTS

| 2,819,999 A * | 1/1958 | Schlichtkrull et al. ......... 514/6.4 |
| 5,457,066 A * | 10/1995 | Frank et al. .................. 435/68.1 |
| 6,001,604 A * | 12/1999 | Hartman et al. ............. 435/68.1 |
| 2011/0117600 A1 * | 5/2011 | Annibali et al. ............. 435/69.4 |

FOREIGN PATENT DOCUMENTS

| EP | 0195691 B1 | 9/1986 |
| GB | 931954 A | 7/1963 |
| WO | 2004044206 A1 | 5/2004 |
| WO | 2007043059 A1 | 4/2007 |
| WO | WO 2007043059 A1 * | 4/2007 |

OTHER PUBLICATIONS

Yang et al "Separation and Characterization of Trypsin and Carboxypeptidase B-Digested Products of Met-Lys-Human Proinsulin". Appl Biochem and Biotech 76:107-114. Published Mar. 1, 1999.*
Kemmler, W. et al, The Journal of Biological Chemistry, Nov. 1971, vol. 246, No. 22, pp. 6786-6791.
Castellanos-Serra, L. R. et al, FEBS Letters, 1996, vol. 378, pp. 171-176.
Nilsson, J. et al, "Integrated production of human insulin and its C-peptide" Journal of Biotechnology, 1996, vol. 48, pp. 241-250.
International Search Report based on International application No. PCT/IN2008/000598.

* cited by examiner

*Primary Examiner* — James H Alstrum Acevedo
*Assistant Examiner* — Zachary J Miknis
(74) *Attorney, Agent, or Firm* — Schwegman Lundberg & Woessner, P.A.

(57) ABSTRACT

The present invention relates to the preparation of insulin compounds including their analogs or derivatives thereof from their corresponding precursor forms by a one step enzymatic reaction involving the combinatorial and concurrent use of optimal quantities of trypsin and carboxypeptidase B that work synergistically directing the reaction in a controlled manner to avoid production of random undesired byproducts. Particularly, the enzymatic conversion reactions of the instant invention offer advantages of reduction in the number operational steps, higher yield and purity of the desired end products.

15 Claims, No Drawings

SEQUENCE LISTING

```
<160> NUMBER OF SEQ ID NOS: 9

<210> SEQ ID NO 1
<211> LENGTH: 67
<212> TYPE: PRT
<213> ORGANISM: Pichia pastoris
<220> FEATURE:
<221> NAME/KEY: PEPTIDE
<222> LOCATION: (1)..(67)

<400> SEQUENCE: 1

Glu Glu Ala Glu Ala Glu Ala Glu Pro Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Asp Lys Thr Arg Asp Ala Asp Arg Gly Ile
        35                  40                  45

Val Glu Gln Cys Cys Thr Ser Ile Cys Ser Leu Tyr Gln Leu Glu Asn
    50                  55                  60
```

Tyr Cys Asn
65

<210> SEQ ID NO 2
<211> LENGTH: 61
<212> TYPE: PRT
<213> ORGANISM: Pichia pastoris
<220> FEATURE:
<221> NAME/KEY: PEPTIDE
<222> LOCATION: (1)..(61)

<400> SEQUENCE: 2

Gly Ala Val Arg Phe Val Asn Gln His Leu Cys Gly Ser His Leu Val
1               5                   10                  15

Glu Ala Leu Tyr Leu Val Cys Gly Glu Arg Gly Phe Phe Tyr Thr Asp
                20                  25                  30

Lys Thr Arg Asp Ala Asp Arg Gly Ile Val Glu Gln Cys Cys Thr
                35                  40                  45

Ser Ile Cys Ser Leu Tyr Gln Leu Glu Asn Tyr Cys Asn
        50                  55                  60

<210> SEQ ID NO 3
<211> LENGTH: 57
<212> TYPE: PRT
<213> ORGANISM: Pichia pastoris
<220> FEATURE:
<221> NAME/KEY: PEPTIDE
<222> LOCATION: (1)..(57)

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Arg Asp
                20                  25                  30

Ala Asp Arg Gly Ile Val Glu Gln Cys Cys Thr Ser Ile Cys Ser
            35                  40                  45

Leu Tyr Gln Leu Glu Asn Tyr Cys Asn
        50                  55

<210> SEQ ID NO 4
<211> LENGTH: 67
<212> TYPE: PRT
<213> ORGANISM: Pichia pastoris
<220> FEATURE:
<221> NAME/KEY: PEPTIDE
<222> LOCATION: (1)..(67)

<400> SEQUENCE: 4

Glu Glu Ala Glu Ala Glu Ala Glu Pro Arg Phe Val Asn Gln His Leu
1               5                   10                  15

Cys Gly Ser His Leu Val Glu Ala Leu Tyr Leu Val Cys Gly Glu Arg
                20                  25                  30

Gly Phe Phe Tyr Thr Lys Pro Thr Arg Asp Ala Asp Arg Gly Ile
            35                  40                  45

Val Glu Gln Cys Cys Thr Ser Ile Cys Ser Leu Tyr Gln Leu Glu Asn
    50                  55                  60

Tyr Cys Asn
65

<210> SEQ ID NO 5
<211> LENGTH: 61
<212> TYPE: PRT

```
<213> ORGANISM: Pichia pastoris
<220> FEATURE:
<221> NAME/KEY: PEPTIDE
<222> LOCATION: (1)..(61)

<400> SEQUENCE: 5
```

Gly Ala Val Arg Phe Val Asn Gln His Leu Cys Gly Ser His Leu Val
1               5                   10                  15

Glu Ala Leu Tyr Leu Val Cys Gly Glu Arg Gly Phe Phe Tyr Thr Lys
            20                  25                  30

Pro Thr Arg Asp Ala Asp Asp Arg Gly Ile Val Glu Gln Cys Cys Thr
        35                  40                  45

Ser Ile Cys Ser Leu Tyr Gln Leu Glu Asn Tyr Cys Asn
    50                  55                  60

```
<210> SEQ ID NO 6
<211> LENGTH: 57
<212> TYPE: PRT
<213> ORGANISM: Pichia pastoris
<220> FEATURE:
<221> NAME/KEY: PEPTIDE
<222> LOCATION: (1)..(57)

<400> SEQUENCE: 6
```

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr Arg Asp
            20                  25                  30

Ala Asp Asp Arg Gly Ile Val Glu Gln Cys Cys Thr Ser Ile Cys Ser
        35                  40                  45

Leu Tyr Gln Leu Glu Asn Tyr Cys Asn
    50                  55

```
<210> SEQ ID NO 7
<211> LENGTH: 67
<212> TYPE: PRT
<213> ORGANISM: Pichia pastoris
<220> FEATURE:
<221> NAME/KEY: PEPTIDE
<222> LOCATION: (1)..(67)

<400> SEQUENCE: 7
```

Glu Glu Ala Glu Ala Glu Ala Glu Pro Arg Phe Val Lys Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Glu Thr Arg Asp Ala Asp Asp Arg Gly Ile
        35                  40                  45

Val Glu Gln Cys Cys Thr Ser Ile Cys Ser Leu Tyr Gln Leu Glu Asn
    50                  55                  60

Tyr Cys Asn
65

```
<210> SEQ ID NO 8
<211> LENGTH: 61
<212> TYPE: PRT
<213> ORGANISM: Pichia pastoris
<220> FEATURE:
<221> NAME/KEY: PEPTIDE
<222> LOCATION: (1)..(61)

<400> SEQUENCE: 8
```

```
Gly Ala Val Arg Phe Val Lys Gln His Leu Cys Gly Ser His Leu Val
1               5                   10                  15
Glu Ala Leu Tyr Leu Val Cys Gly Glu Arg Gly Phe Phe Tyr Thr Pro
                20                  25                  30
Glu Thr Arg Asp Ala Asp Asp Arg Gly Ile Val Glu Gln Cys Cys Thr
            35                  40                  45
Ser Ile Cys Ser Leu Tyr Gln Leu Glu Asn Tyr Cys Asn
    50                  55                  60

<210> SEQ ID NO 9
<211> LENGTH: 57
<212> TYPE: PRT
<213> ORGANISM: Pichia pastoris
<220> FEATURE:
<221> NAME/KEY: PEPTIDE
<222> LOCATION: (1)..(57)

<400> SEQUENCE: 9

Phe Val Lys Gln His Leu Cys Gly Ser His Leu Val Glu Ala Leu Tyr
1               5                   10                  15
Leu Val Cys Gly Glu Arg Gly Phe Phe Tyr Thr Pro Glu Thr Arg Asp
                20                  25                  30
Ala Asp Asp Arg Gly Ile Val Glu Gln Cys Cys Thr Ser Ile Cys Ser
            35                  40                  45
Leu Tyr Gln Leu Glu Asn Tyr Cys Asn
    50                  55
```

PROCESS FOR PREPARATION OF INSULIN COMPOUNDS

FIELD OF THE INVENTION

The present invention relates to the preparation of insulin compounds including their analogs or derivatives thereof from their corresponding precursor forms by a one step enzymatic reaction involving the combinatorial and concurrent use of optimal quantities of trypsin and carboxypeptidase B that work synergistically directing the reaction in a controlled manner to avoid production of random undesired byproducts. Particularly, the enzymatic conversion reactions of the instant invention offer advantages of reduction in the number operational steps, higher yield and purity of the desired end products.

BACKGROUND AND PRIOR ART OF THE INVENTION

Genetic engineering methods are increasingly allowing precursor forms of insulin to be expressed in microorganisms (EP-A-347 781, EP-A-367 163). The pre pro sequences are usually cleaved off chemically and/or enzymatically (DE-P-3 440 988, EP-A-0264250). Known enzymatic conversion methods are based on cleavage with trypsin and carboxypeptidase B (Kemmler W. et al. J. Biol. Chem., 246 (1971) 6786-6791; EP-A-195 691; EP-B-89007). In the typical process of conversion of Insulin precursor molecule to the corresponding molecule, the linker peptide between the A and B chains are removed. The enzymatic reactions with trypsin is an enzymatic and complex reaction that cleaves not only those peptide bonds whose cleavage produces human insulin or the desired end products but also, in a competing reaction, cleavage at other susceptible sites produce a plurality of undesired byproducts.

Prior art methods include the use of trypsin and a second enzyme carboxypeptidase in such manner that the second enzyme carboxypeptidase is added when the required intermediate will be formed in the reaction. The disadvantage of these methods is the formation of large amounts of impurity byproducts which can be removed from the reaction solution only with difficulty. In the particular case of the conversion of human precursor form of into human insulin (human insulin, HI), there is formation of large amounts of des-Thr(B30)-human insulin (des-Thr(B30)-HI).

From the above, it is evident that it would be advantageous to follow a simpler enzymatic reaction process for cleavage of precursor insulin compounds, their analogs and derivatives thereof to insulin through a much simpler step that removes the possible formations of polymeric impurities as completely as possible and, at the same time, increases the concentration of desired insulin end product as much as possible. An additional condition is the need to ensure a high yield overall enhancing the ease of operation, quality as well as the quantity of the desired end product.

The disadvantages of the known processes have been remedied by the enzymatic reactions carried out in the instant invention, and it has turned out that the increase in yield without undesired byproducts is relative to the optimal concentration of trypsin and carboxypeptidase used under conducive reaction conditions. The inventors have endeavored to develop an improved one step enzymatic reaction process involving the combinatorial and concurrent use of optimal quantities of trypsin and carboxypeptidase B that work synergistically to provide the desired end products enhancing the ease of operation, purity and yield of the end products.

OBJECTIVES OF THE INVENTION

The main objective of the present invention is to obtain a process for preparation of insulin compounds and its analogs or derivatives from their corresponding precursors with minimal formation of undesired by-products that is enabled by a one step enzymatic reaction involving the combinatorial and concurrent use of optimal quantities of trypsin and carboxypeptidaseB working synergistically to provide the desired end products.

Another main objective of the present invention is to provide an insulin analog precursor as represented by the SEQ IDs 1, 2, 3, 4, 5, 6, 7 and 8 that may be used as the starting material said precursors may either be in liquid or crystal form.

Yet another objective of the present invention is to provide an expression vector for the expression of proinsulin or its analogs or derivatives that comprises said respective DNA sequence that codes for the precursor molecule.

Still another objective of the present invention is to provide a suitable microorganism/host that is transformed with said expression vector and subsequently provides a process for preparing respective insulin compounds, which comprises culturing said transformed microorganism in a suitable fermentation medium and fermenting conditions to produce precursor insulin forms Still another objective of the present invention includes the method of converting the insulin compounds precursor forms to their respective active forms through a single step enzyme reaction wherein trypsin and carboxypeptidase are added together in optimal quantities that permit synergistic and a controlled reaction minimizing the production of unwanted end products.

Still another objective of the present invention is to obtain a process for obtaining a insulin or its analog or derivatives thereof from their respective precursor counterparts comprising successively carrying out the steps in a sequential order.

Still another objective of the present invention is to obtain an insulin molecule.

Still another objective of the present invention is to obtain an insulin molecule selected from the group comprising insulin, lispro, aspart, glulisine or IN-105.

STATEMENT OF THE INVENTION

Accordingly, the present invention relates to a process for preparation of insulin compounds and its analogs or derivatives from their corresponding precursors Which comprises treating said precursor with trypsin and carboxypeptidase used combinatorially and concurrently provided that the relative concentration ratio of trypsin to carboxypeptidase is from about 5:1 to about 50:1; a process for obtaining a insulin or its analog or derivatives thereof from their respective precursor counterparts comprising successively carrying out the following steps in the following sequential order (a) dissolving optimal amount of the precursor of insulin or an insulin derivative in a buffer solution; (b) preparing various aliquots of the precursor solution at pH ranges of about 7.0 to 9.0; (c) introducing the enzymes trypsin and carboxypeptidase concurrently to the various aliquots prepared as in Step (b) and incubating the mixture for about 4-10 hours; (d) precipitating the desired insulin product by addition of citric acid buffer

BRIEF DESCRIPTION OF ACCOMPANYING SEQUENCE LISTINGS

SEQ ID 1: Amino acid sequence of the Aspart precursor molecule.
SEQ ID 2: Amino acid sequence of the Aspart precursor molecule.
SEQ ID 3: Amino acid sequence of the Aspart precursor molecule.
SEQ ID 4: Amino acid sequence of the Lispro precursor molecule.
SEQ ID 5: Amino acid sequence of the Lispro precursor molecule.
SEQ ID 6: Amino acid sequence of the Lispro precursor molecule.
SEQ ID 7: Amino acid sequence of the Glulisine precursor molecule.
SEQ ID 8: Amino acid sequence of the Glulisine precursor molecule.
SEQ ID 9: Amino acid sequence of the Glulisine precursor molecule.

DETAILED DESCRIPTION OF THE INVENTION

The present invention relates to a process for preparation of insulin compounds and its analogs or derivatives from their corresponding precursors represented by the formula:

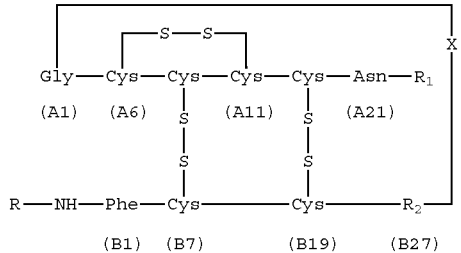

where,
- R is hydrogen or a chemically or enzymatically cleavable amino acid residue or a chemically or enzymatically cleavable peptide comprising at least two amino acid residues.
- $R_1$ is OH or an amino acid residue, or $Y_1$-$Y_2$ in which Y is an amino acid residue.
- The moieties A1 to A21 corresponds to insulin A chain and the moieties B1 to B27 corresponds to insulin B chain including amino acid substitution, deletion and/or additions thereof.
- $R_2$ is $Z_1$-$Z_2$ wherein $Z_1$ is selected from Pro, Lys, Asp and $Z_2$ is selected from Lys or Pro or Glu or $Z_1$-$Z_2$-$Z_3$ wherein $Z_1$ is selected from Pro, Lys, Asp and $Z_2$ is selected from Lys or Pro or Glu and $Z_3$ is threonine or a peptide moiety of at least three amino acid residues with the provision that the amino acid corresponding to B30 is threonine.
- X is a polypeptide that connects the A chain to the B chain which can be cleaved enzymatically without disrupting either the A chain or the B chain bearing at least two amino acids wherein the first and the last amino acid is Lysine or Arginine.

Which comprises treating said precursor with trypsin and carboxypeptidase used combinatorially and concurrently provided that the relative concentration ratio of trypsin to carboxypeptidase is from about 5:1 to about 50:1.

In another embodiment of the present invention the respective precursor molecule comprises an amino acid sequence which is at least 85% homologous to the amino acid sequence as set forth in SEQ IDs 1, 2, 3, 4, 5, 6, 7, 8 and 9.

In another embodiment of the present invention the relative amount of trypsin to that of the insulin precursor ranges from about 1:10 to about 1:500.

In yet another embodiment of the present invention the wherein the relative amount of trypsin to that of the insulin precursor is about 1:100.

In still another embodiment of the present invention the relative amount of carboxypeptidase to that of the insulin precursor is about 1:500.

In still another embodiment of the present invention the relative concentration ratio of trypsin to carboxypeptidase is from about 5:1 to about 50:1.

In still another embodiment of the present invention the relative concentration ratio of trypsin to carboxypeptidase is about 5:1.

In still another embodiment of the present invention the concentration of trypsin used for the conversion reaction is at least 0.01 mg/ml.

In still another embodiment of the present invention the concentration of carboxypeptidase used for the conversion reaction is at least 0.001 mg/ml.

In still another embodiment of the present invention the precursor is either in liquid or crystal form.

In still another embodiment of the present invention the conversion reaction is carried out at a pH of 6.5 to 10.

In still another embodiment of the present invention the conversion reaction is carried out at a pH of 7 to 9.

In still another embodiment of the present invention the conversion reaction is carried out at a temperature ranging from about 2° C. to 40° C.

In still another embodiment of the present invention the duration of the enzymatic conversion reaction is about 2 to 24 hours.

In still another embodiment of the present invention the reaction medium contains at least 30% water or a water miscible solvent.

In still another embodiment of the present invention the water miscible solvent is selected from the group comprising methanol, ethanol, acetone or N,N-dimethylformamide.

In still another embodiment of the present invention the reaction medium further comprises a salt acting as a buffering agent.

In still another embodiment of the present invention the salt is selected from the group comprising TRIS, ethylenediamine, triethanolamine, glycine, HEPES (N-2-hydroxy-ethylpiperazine-N'-2-ethanesulfonic acid).

In still another embodiment of the present invention the concentration of salt used in the reaction medium is about 10 mM to 1 M.

In still another embodiment of the present invention the concentration of salt used in the reaction medium is about 0.6 M.

The present invention relates to a process for obtaining a insulin or its analog or derivatives thereof from their respective precursor counterparts comprising successively carrying out the following steps in the following sequential order
(a) Dissolving optimal amount of the precursor of insulin or an insulin derivative in a buffer solution.

(b) Preparing various aliquots of the precursor solution at pH ranges of about 7.0 to 9.0.

(c) Introducing the enzymes trypsin and carboxypeptidase concurrently to the various aliquots prepared as in Step (b) and incubating the mixture for about 4-10 hours.

(d) Precipitating the desired insulin product by addition of citric acid buffer and ZnCl$_2$.

The present invention relates to an insulin molecule prepared according to any of the preceding claims.

The present invention relates to an insulin molecule prepared according to any of the preceding claims selected from the group comprising insulin, lispro, aspart, glulisine or IN-105.

Reference will now be made in detail to the presently preferred embodiments of the invention which, together with the following example, serve to explain the principles of the invention.

In describing and claiming the present invention, the following terminology will be used in accordance with the definitions set out herein.

Unless otherwise defined herein, scientific and technical terms used in connection with the present invention shall have the meanings that are, commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques described herein are those well known and commonly used in the art. The methods and techniques of the present invention are generally performed according to conventional methods well known in the art.

As used herein "amino acid" refers to peptide or protein sequences or portions thereof. The terms "protein", "peptide" and "polypeptide" are used interchangeably.

Herein, the term "insulin" covers insulin from any species such as porcine insulin, bovine insulin, and human insulin and complexes thereof such as zinc complexes including dimers and oligomers, for example, hexamers thereof. Additionally, the term "insulin" herein covers so-called "insulin analogues". An insulin analogue is an insulin molecule having one or more mutations, substitutions, deletions and/or additions of the A and/or B amino acid chains relative to the native human insulin molecule. More specifically, one or more of the amino acid residues may have been exchanged with another amino acid residue and/or one or more amino acid residue may have been deleted and/or one or two amino acid residues may have been added, with the provision that said insulin analog has a sufficient insulin activity. The insulin analogs are preferably such wherein one or more of the naturally occurring amino acid residues, preferably one, two, or three of them, have been substituted by another codable amino acid residue. Examples of insulin analogues are described in the following patents and equivalents thereto: U.S. Pat. No. 5,618,913, EP 254,516, EP 280,534, U.S. Pat. No. 5,750,497 and U.S. Pat. No. 6,011,007. Examples of specific insulin analogues are insulin aspart (i.e., AspB28 human insulin) and insulin lispro (i.e., LysB28, ProB29 human insulin) and "insulin glulisine" (Lys B(3), Glu B(29) human insulin.

One aspect of the invention relates to insulin precursor compounds represented by the following formula:

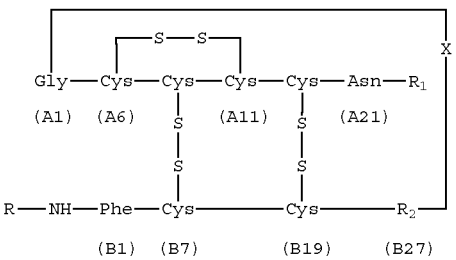

where,

R is hydrogen or a chemically or enzymatically cleavable amino acid residue or a chemically or enzymatically cleavable peptide comprising at least two amino acid residues.

$R_1$ is OH or an amino acid residue, or $Y_1$-$Y_2$ in which Y is an amino acid residue.

The moieties $A_1$ to $A_{21}$ corresponds to insulin A chain and the moieties $B_1$ to $B_{27}$ corresponds to insulin B chain including amino acid substitution, deletion and/or additions thereof.

R2 is $Z_1$-$Z_2$ wherein $Z_1$ is selected from Pro, Lys, Asp and $Z_2$ is selected from Lys or Pro or Glu or $Z_1$-$Z_2$-$Z_3$ wherein $Z_1$ is selected from Pro, Lys, Asp and $Z_2$ is selected from Lys or Pro or Glu and $Z_3$ is threonine or a peptide moiety of at least three amino acid residues with the provision that the amino acid corresponding to B30 is threonine.

X is a polypeptide that connects the A chain to the B chain which can be cleaved enzymatically without disrupting either the A chain or the B chain bearing at least two amino acids wherein the first and the last amino acid is Lysine or arginine.

One of the aspect of the instant invention specifically relates to the molecule IN-105. IN-105 is an insulin molecule conjugated at the epsilon amino acid Lysine at position B29 of the insulin B-chain with an ampiphilic oligomer of structural formula $CH_3O$—$(C_4H_2O)_3$—$CH_2$—$CH_2$—COON. The molecule may be monoconjugated at A1, B1 and B29, diconjugated at various combinations of A1, B1 and B29, or triconjugated at various combinations of A1, B1 and B29.

In one aspect, the isolated insulin precursor molecule which comprises an amino acid sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to a polypeptide molecule as represented by SEQ IDs 1, 2, 3, 4, 5 and 6.

Trypsin is a typical serine protease and hydrolyzes a protein or a peptide at the carboxyl terminal of an arginine or lysine residue (Enzymes, pp 261-262 (1979), ed. Dixon, M. & Webb, E. C., Longman Group Ltd., London). In particular, facile hydrolysis occurs at a dibasic site where two successive arginine or lysine residues exist, and it is known that hydrolysis occurs most readily where the dibasic site is located in or next to a β-turn structure (Rholam, M., et al., FEBS Lett., 207, 1-6 (1986). The Enzyme Vol. H, 3rd Edition, Editor Boyer, Acad. Press NY. Pp. 249-275). Particularly, trypsin cleaves peptide bonds at C-terminal arginine (Arg) or lysine (Lys) residues. Tryptic cleavage of insulin precursor molecules can occur at different cleavage sites simultaneously. Because of the many cleavage sides within a specific insulin precursor molecule, many undesired side-products can be formed during tryptic cleavage reaction.

Recombinant porcine pancreatic trypsin has a molecular weight of about 23,000 daltons and an enzymatic activity optimum at pH 8.0. Trypsin is used in the industrial process of producing insulin and insulin analogs. The production of these biomolecules is described in the literature and several approaches have been chosen.

Carboxypeptidase B preferentially hydrolyzes the basic amino acids lysine, arginine and ornithine from the C-terminal position of polypeptides. Carboxypeptidase B is an exopeptidase catalyzing a hydrolytic release of the C-terminal basic amino acid residues of arginine and lysine from peptides and proteins.

The term "C-peptide" or "linker peptide" as used herein includes all forms of insulin C-peptide, including native or synthetic peptides. Such insulin C-peptides may be human peptides, or may be from other animal species and genera, preferably mammals. Thus variants and modifications of native insulin C-peptide are included as long as they retain insulin C-peptide activity. It is known in the art to modify the sequences of proteins or peptides, whilst retaining their useful activity and this may be achieved using techniques which are standard in the art and widely described in the literature e.g. random or site-directed mutagenesis, cleavage and ligation of nucleic acids etc. Thus, functionally equivalent variants or derivatives of native insulin C-peptide sequences may readily be prepared according to techniques well known in the art, and include peptide sequences having a functional, e.g. a biological, activity of a native insulin C-peptide. All such analogues, variants, derivatives or fragments of insulin C-peptide are especially included in the scope of this invention, and are subsumed under the term "an insulin C-peptide".

The main requirements of a C-peptide are that they be of sufficient length to permit a di-sulphide bond formation between the A- and B-chains and they can be cleavable from the insulin precursor leading to insulin formation. A typical di-peptide used as a C-peptide is -Arg-Arg-. C-peptides may be of any length which start with Arg or Lys and end with Arg or lys.

The invention provides vectors comprising DNA encoding any of the herein described genes. Host cell comprising any such vectors are also provided. By way of example, the host cells may be bacterial, fungal, or mammalian.

The invention employs a recombinant host cell in which at least a portion of a nucleic acid sequence expressing the insulin compound precursor is produced. A recombinant expression system is selected from prokaryotic and eukaryotic hosts. Eukaryotic hosts include yeast cells (e.g., *Saccharomyces cerevisiae* or *Pichia pastoris*), mammalian cells or plant cells. Bacterial and eukaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells. The choice of the expression system depends on the features desired for the expressed polypeptide.

Most preferably related to aspects to the present inventions, the most preferred host cells are methylotrophic yeasts. Strains of a methylotrophic yeast which can be modified using the present invention include, but are not limited to, yeast strains capable of growing on methanol, such as yeasts of the genera *Pichia, Candida, Hansenula*, or *Torulopsis*. Preferred methylotrophic yeasts are of the genus *Pichia*. Methylotrophic yeast strains which can be modified using the present methods also include those methylotrophic yeast strains which have been engineered to express one or more heterologous proteins of interest. The most preferred host cell according to the aspect of the present invention is *Pichia pastoris* is GS115.

The host cell or organism can be engineered to express recombinant protein or peptide using standard techniques. For example, recombinant protein can be expressed from a vector or from an exogenous gene inserted into the genome of the host.

Vectors that can be used to express exogenous proteins are well known in the art and are described below. Preferred vectors of the present invention carrying insulin precursor molecule genes include but are not limited to pPIC9K.

The most significant aspect of the instant invention relates to a process for converting an insulin compounds and its analogs or derivatives from their corresponding precursors represented by the formula

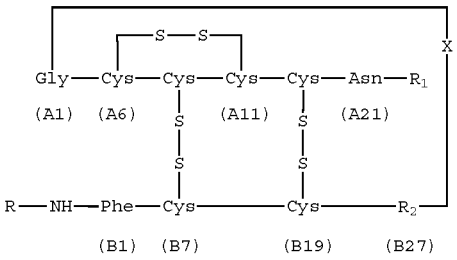

where,

R is hydrogen or a chemically or enzymatically cleavable amino acid residue or a chemically or enzymatically cleavable peptide comprising at least two amino acid residues.

$R_1$ is OH or an amino acid residue, or $Y_1$-$Y_2$ in which Y is an amino acid residue.

The moieties A1 to A21 corresponds to insulin A chain and the moieties B1 to B27 corresponds to insulin B chain including amino acid substitution, deletion and/or additions thereof.

$R_2$ is $Z_1$-$Z_2$ wherein $Z_1$ is selected from Pro, Lys, Asp and $Z_2$ is selected from Lys or Pro or Glu or $Z_1$-$Z_2$-$Z_3$ wherein $Z_1$ is selected from Pro, Lys, Asp and $Z_2$ is selected from Lys or Pro or Glu and $Z_3$ is threonine or a peptide moiety of at least three amino acid residues with the provision that the amino acid corresponding to B30 is threonine.

X is a polypeptide that connects the A chain to the B chain which can be cleaved enzymatically without disrupting either the A chain or the B chain bearing at least two amino acids wherein the first and the last amino acid is Lysine or Arginine.

which comprises treating said precursor with trypsin and carboxypeptidase used combinatorially and concurrently provided that the relative concentration ratio of trpsin to carboxypeptidase is from about 5:1 to about 50:1.

The precursor molecule may either be in a liquid or crystal form.

The process of conversion of the insulin precursor molecule to their corresponding insulin molecule is conducted in an aqueous medium comprising at least about 40% water; it does not, however preclude the presence of at least about 30%, or about 50% or about 60% or about 70% or about 80% water and also the presence of water-miscible solvents such as methanol, ethanol, acetone, N,N-dimethylformamide and the like.

The reaction medium may additionally comprise any salt with buffering properties. Preferably, the reaction medium comprises Tris as a salt in the concentration ranging from 10 mM to 1 M. Most preferably the concentration of Tris used in the reaction medium is 0.6 M.

The conversion is carried out at any of the wide range of temperatures, generally from about 0° C. to 40° C. Preferably the reaction is conducted at a temperature of from about 10° C. to about 30° C. and most preferably from about 15° C. to about 25° C.

The pH of the reaction mixture can range anywhere from about 2 to about 12. However, best results are obtained by careful pH control such that the reaction progresses at a pH range of about 6.5 to 10. Preferably the reaction occurs at a pH range of 7 to 9.5, preferably from about 8 to 9, and when precisely controlled at pH 8.5.

The pH control is controlled by the use of a buffering agent. Any of the of wide range of suitable buffers used include TRIS, ethylenediamine, triethanolamine, glycine, HEPES (N-2-hydroxy-ethylpiperazine-N'-2-ethanesulfonic acid), and the like.

The amount of Trypsin and Carboxypeptidase B that generally is used is related both as between the two enzymes and to the amount of the insulin precursor molecule. The enzymes can be incorporated in the reaction mixtures either in solution or using recognized techniques such immobilization on a suitable support and thereby made available in the reaction medium.

On a weight:weight basis, trypsin generally will be present in an amount relative to that of the insulin precursor ranging from about 1:10 to about 1:500, preferably, from about 1:10 to about 1:200, most preferably from about 1:10 to about 1:100 or 1:10 to about 1:50 or about 1:10 to about 1:25. The most preferred concentration of trypsin relative to the concentration of insulin employed is 1:100. The concentration of trypsin used for the conversion reaction is at least 0.01 mg/ml.

On a weight:weight basis, carboxypeptidase B generally will be present in an amount relative to that of the insulin precursor ranging from about 1:500 or about 3:500. The most preferred concentration of carboxypeptidase relative to the concentration of insulin employed is 1:500. The concentration of carboxypeptidase used for the conversion reaction is at least 0.001 mg/ml.

According to another significant parameter of the present invention is the ratio of the trypsin to carboxypeptidase B in the reaction mixture. Generally, on a weight basis, the ratio of trypsin to carboxypeptidase B is in range of 5:1 to 50:1. Preferably, on a weight basis, the ratio of trypsin to carboxypeptidase B is about 50:3 to about 5:3. The most preferred ratio of trypsin to carboxypeptidase B is about 5:1:

The duration of the reaction may range from about 2 to 48 hours, preferably the duration of the reaction is about 2 to 24 hours.

Accordingly, the present invention relating to a process for obtaining a insulin or its analog or derivatives thereof from their respective precursor counterparts comprises successively carrying out the following steps in a sequential order as provided below:
  (a) Dissolving optimal amount of the of the precursor of insulin or an insulin derivative in a buffer solution.
  (b) Preparing various aliquots of the precursor solution at pH ranges of about 7.0 to 9.0.
  (c) Introducing the enzymes trypsin and carboxypeptidase concurrently to the various aliquots prepared as in Step (b) and incubating the mixture for about 4-10 hours.
  (d) Precipitating the desired insulin product by addition of citric acid buffer and $ZnCl_2$.

The preferred embodiment of the invention is described below in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The description of a preferred embodiment and best mode of the invention known to the applicant at the time of filing the application has been presented and is intended for the purposes of illustration and description only. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

The invention is further elaborated with the help of following examples. However, these examples should not be construed to limit the scope of the invention.

Example 1A

Aspart Precursor (Seq ID 1, 2 and 3)

Aspart precursor of Formula X-[Aspart B chain (B1-B30)]-Y-[Aspart A chain (A1-A21)], where X is a leader peptide sequence, B chain is Aspart B chain sequence of B1-B30, Y is a linker peptide sequence between B chain and A chain, A chain is the A-chain of Aspart. The sequence may be devoid of leader or other leader peptide (e.g. EEAEAE-AEPR or GAVR). The linker peptide Y can be anyone from the example R, and RDADDR.

The precursor sequence is represented by SEQ IDs 1 and 2. The precursor may be produced by any suitable expression system such as *Escherichia coli, Pichia pastoris, Saccharomyces cerevisiae*, CHO cells etc.

The Aspart precursor was cloned in frame with the Mat-alfa signal peptide in *Pichia* expression vector, pPIC9K.

Pichia pastoris host strain GS115 was transformed with the recombinant plasmid to obtain clone expressing Aspart precursor.

Aspart precursor is secreted by Pichia pastoris into the culture medium. The broth is centrifuged and cells are separated from the supernatant. There are multiple options available for the capture of the precursor including Ion-Exchange chromatography and Hydrophobic chromatography. For this invention cation-exchange chromatography and HIC were used to capture the specific precursor.

Example 1B

Lispro Precursor (Seq ID 3, 4 and 5)

Lispro precursor of Formula X-[Lispro B chain (B1-B30)]-Y-[Lispro A chain (A1-A21)], where X is a leader peptide sequence, B chain is Lispro B chain sequence of B1-B30, Y is a linker peptide sequence between B chain and A chain, A chain is the A-chain of Lispro. The sequence may be devoid of leader or other leader peptide. The linker peptide Y can be anyone from the example R, or RDADDR. The precursor sequence is represented by SEQ IDs 3 and 4. The precursor may be produced by any suitable expression system such as Escherichia coli, Pichia pastoris, Saccharomyces cerevisiae, CHO cells etc.

The Lispro precursor was cloned in frame with the Mat-alfa signal peptide in Pichia expression vector, pPIC9K. Pichia pastoris host strain GS115 was transformed with the recombinant plasmid to obtain clone expressing Lispro precursor.

Lispro precursor is secreted by Pichia pastoris into the culture medium. The broth is centrifuged and cells are separated from the supernatant. There are multiple options available for the capture of the precursor including Ion-Exchange chromatography and Hydrophobic chromatography. For this invention cation-exchange chromatography and HIC were used to capture the specific precursor.

Example 1C

Glulisine Precursor (Seq ID 5, 6 and 7)

Glulisine precursor of Formula X-[Glulisine B chain (B1-B30)]-Y-[Glulisine A chain (A1-A21)], where X is a leader peptide sequence, B chain is Glulisine chain sequence of B1-B30, Y is a linker peptide sequence between B chain and A chain, A chain is the A-chain of Glulisine. The sequence may be devoid of leader or other leader peptide. The linker peptide Y can be anyone from the example R, or RDADDR. The precursor sequence is represented by SEQ IDs 5 and 6. The precursor may be produced by any suitable expression system such as Escherichia coli, Pichia pastoris, Saccharomyces cerevisiae, CHO cells etc. The Glulisine precursor was cloned in frame with the Mat-alfa signal peptide in Pichia expression vector, pPIC9K. Pichia pastoris host strain GS115 was transformed with the recombinant plasmid to obtain clone expressing Glulisine precursor.

Glulisine precursor is secreted by Pichia pastoris into the culture medium. The broth is centrifuged and cells are separated from the supernatant. There are multiple options available for the capture of the precursor including Ion-Exchange chromatography and Hydrophobic chromatography. For this invention cation-exchange chromatography and HIC were used to capture the specific precursor.

Precursor Crystallization

The different insulin compound precursor captured from the fermentation broth by using a cation-exchange chromatography step was crystallised for the purpose of colour removal and storage. The crystallisation was done such that the precursor concentration at the start of crystallisation was around 2 to 20 g/L, preferably 8 to 14 g/L. The crystallisation was done by adding $ZnCl_2$ & phenol and then adjusting the pH to between 3.0 and 8.0, preferably between 3.5 and 5.5. Phenol can be added at 0.1 to 0.5% of the CIEX elution pool volume. A 4% $ZnCl_2$ solution can be added at 3 to 15% of the CIEX elution pool volume. The pH can be adjusted by using any alkali, preferably NaOH or TRIS. The crystallisation process can be done at a temperature between 2 and 30° C. and the slurry is stored for some time so that the crystals will be formed completely. The precursor crystals can be separated from the supernatant by either centrifugation or decantation.

Example 2A

Example of Precursor Lispro Crystallization 463 ml of elution pool (precursor concentration 13.8 g/L) was taken and 2.315 ml of phenol (0.5% of EP volume) was added after proper thawing. This was followed by addition of 57.875 ml of 4% $ZnCl_2$ solution (12.5% of EP volume). The pH was 4.08 at this stage and it was adjusted to 4.8 by adding 420 ml of 2.5N NaOH. The mother liquor was kept under slow stirring conditions for 15 minutes and then transferred to cold room (2-8° C.), where it was kept overnight. Then the whole mixture was centrifuged at 5000 rpm for 20 minutes in a Beckman Coulter AVANTI J-26 XP centrifuge (high performance centrifuge system). The loss in supernatant was 1.55%.

Example 2B

Example of Precursor Aspart Crystallization 500 ml of elution pool (precursor concentration 2.9 g/L) was taken and 0.625 ml of phenol (0.125% of EP volume) was added after proper thawing. This was followed by addition of 15.625 ml of 4% $ZnCl_2$ solution (3.125% of EP volume). The pH was 4.08 at this stage and it was adjusted to 4.8 by adding 315 ml of 2.5N NaOH. The mother liquor was kept under slow stirring conditions for 15 minutes and then transferred to cold room (2-8° C.), where it was kept for five hours. Then the supernatant was separated by centrifugation. The loss in supernatant was 4%.

Example 2C

Example of Precursor Glulisine Crystallization 250 ml of elution pool from the Sp sepharose run of Precursor Glulisine (precursor concentration 3.8 g/L) was taken and 0.31 ml of phenol (0.125% of EP volume) was added after proper thawing. This was followed by addition of 7 ml of 4% $ZnCl_2$ solution (3% of EP volume). The pH was 4.13 at this stage and it was adjusted to 4.9 by adding 2.5N NaOH. The mother liquor was kept under slow stirring conditions for 30 minutes and then transferred to cold room (2-8° C.), where it was kept for five hours. Then the supernatant was separated by centrifugation. The loss in supernatant was 7%.

Example 3A

Enzyme Reactions

Different Insulin compounds can be prepared from their corresponding precursor through an enzymatic conversion. Direct conversion from the precursor to the final product can be obtained by the presence of two protease enzymes. The enzyme reactions were carried out in two different ways. 1st the precursor has to be treated with trypsin or trypsin-like enzymes of plant, animal or microbial recombinant origin. When the Trypsin reaction is over the intermediate in the same reaction mixtures were treated with the 2nd protease enzyme Carboxypeptidase B or similar enzyme of plant, animal, microbial recombinant origin. Carboxypeptoidase B can act on the basic amino acid in the C-terminal end. Alternatively, the Trypsin and Carboxypeptidase enzymes were added in the reaction mixture as a cocktail (together) and the reactions were allowed to continue till the optimum corresponding product formation happened.

Example 4A

When Only Trypsin was Added to the Individual Precursor Reaction Mixture 2 gm of individual Aspart, Lispro and Glulisine precursor crystals were solubilized with 5 ml of 6 M TRIS solution. Product concentration of the individual reaction mixture was kept as 3-5 mg/ml. The pH of the reaction mixture was adjusted to 8.5. Trypsin was added to the individual reaction mixture at a concentration of 50 µg/ml. The reactions were carried out at both 4±0.5° C. and room temperature (24±0.5° C.). It was observed the chromatographic profile at the end of the reaction mixture does not change with respect to reaction temperature but the time for completion of the reaction decreases as the temperature increases. The temperature for the reactions was kept at 24±0.5° C. The reactions were continued for 8 hr and at the end of 8 hr the samples were analyzed.

Similar way the individual precursor of Aspart, Lispro and Glulisine were solubilized in Tris solution and 50% of solvent Dimethyl Formamide at concentration of 3-5 mg/ml. The pH of the reaction mixture was adjusted to 8.5 and the temperature of the reaction mixture was maintained at 24±0.5° C. Trypsin was added to the individual reaction mixture at a concentration of 50 µg/ml.

Observation:

Aspart precursor has been converted to B-30 Des-Threonine Aspart and Des Octapeptide Insulin. Percentage of Des threonine Aspart was 45%, desoctapeptide Insulin was 36%. The formation of required intermediate, Aspart with extra Arginine residue in the B31 position, is around 10-14%. Thus even the 2nd enzyme Carboxypeptidase B be added to the reaction mixture, overall yield for making the final product would be <10-15%.

Similar product profile was found when the reaction was carried out with 50% solvent. But the reaction rate is very slow in presence of solvent. To achieve the similar type of profile the reactions has to continue for almost 18 hrs.

Thus the generation of Aspart from the corresponding precursor through the successive protease reaction could not be possible. Thus it was understood that B-29Lys of Aspart is the most potent site for Trypsin cleavage and as the reaction continues, B-22Arg site are also become prone for Trypsin cleavage and at the end of the reaction we get a mixed population of B-30 des Threonine and Des-Octapeptide in each individual precursor. The cleavage product at B-31 Arginine is very low in all of the precursor product.

Lispro precursor, under similar condition, was converted to Lispro product with extra Arginine residue in the B31 position along with high amount of Des-octapeptide Insulin. Similar type of observation was found when Glulisine Precursor was treated with Trypsin under identical conditions. But the chromatographic profiles of the reaction mixture were not clean at all in case of Lispro and Glulisine precursor. This suggest even the possible final product, Lispro and Glulisine, can be made through the successive reaction with the $2^{nd}$ protease Carboxypeptidase B but the overall yield would be very poor.

Presence of 50% Di-methyl Formamide only slows down the reaction rate in case of Lispro as well as Glulisine precursor.

To check the concept similar type of Trypsin reaction was tried to the IN-105 precursor B-29Lys residue when precursor was blocked in In-105 precursor by the short chain PEG molecule as well as with the nonconjugated precursor molecule. It was observed that in case of conjugated IN-105 precursor, Trypsin cleaves more preferentially at the c-terminal end of Arginine residue of the 31st amino acid to generate IN-105 with an extra Arginine residue in the C-terminal end of B chain. Along with the B-31 Arginine IN-105 Des Octa Insulin is also generated in this reaction mixture. But when the nonconjugated IN-105 precursor was treated with Trypsin, the protease cleaves preferentially at the C-terminal end B-29 Lysine residue to generate Des-Threonine Insulin. The chromatographic profile at the end of the reaction is same both in presence or absence of any solvent in the reaction mixture. It was observed that presence of solvent slows down the reaction rate.

Examples 4B

In the next phase of the experimental conditions, the reactions were carried out by adding Trypsin and Carboxypeptidase B together in the individual precursor reaction mixture.

The concentration of the precursor was generally about 5 to 50 g/L. The reaction was carried out at about pH 5 to 12, preferably about pH 8 to 10. Reaction temperature was about 0-40° C., preferably about 2-25° C. Trishydroxylmethylaminomethane (TRIS) or other buffer systems were used at different ionic strengths to maintain the required pH. Reaction time was variable and was affected by other reaction conditions. Reaction was continued until the purity of the product starts decreasing due to the hydrolysis of the product. It takes generally about 30 minutes to 24 hours and in most cases about 4 to 10 hours.

The concentration of enzyme was determined depending on concentration of substrates and enzyme activity. For example, the crystalline trypsin available in the market was used preferably in a concentration about 10 to 100 mg/L.

Example: 4B (I)

4 gm of Aspart precursor crystal was dissolved in 20 ml of 1M TRIS solution. Product concentration of the solution was maintained to 5 mg/ml and TRIS concentration was maintained to 0.6 M by adding. Aliquots of certain amounts were taken by adjusting the pH of the reaction mixture by 2.5N NaOH or 2N Glacial acetic acid. Aliquots of the reaction mixture at pH 7.0, 7.5, 8.0, 8.5, 9.0 were prepared. 1 ml each of this reaction mixture was taken into each tube as an individual reaction mixture at different condition. The reaction was carried out in all the samples by adding trypsin and Carboxypeptidase B together at different concentrations. The different parameters varied are tabulated.

Constant Parameters:
Product concentration 5 g/L
TRIS buffer concentration 0.6 M
Varied Parameters:
Trypsin concentration: 25-500 mg/L
Carboxypeptidase concentration: 10-30 mg/L
pH: 7.0-9.0.

| Precursor concentration (g/L) | Tris concentration (M) | Trypsin concentration mg/L | Carboxypeptidase B concentration (mg/L) | pH | Yield (%) |
|---|---|---|---|---|---|
| 5 | 0.6 | 500 | 10 | 7.0 | 53 |
| | | | | 8.0 | 66 |
| | | | | 9.0 | 17.5 |
| | | | 30 | 7.0 | 54 |
| | | | | 8.0 | 64 |
| | | | | 9.0 | 16 |
| | | 200 | 10 | 7.0 | 51 |
| | | | | 8.0 | 59 |
| | | | | 9.0 | 24 |
| | | | 30 | 7.0 | 28 |
| | | | | 8.0 | 65 |
| | | | | 9.0 | 64 |
| | | 50 | 10 | 7.5 | 44 |
| | | | | 8.0 | 68 |
| | | | | 8.5 | 75 |
| | | | 30 | 7.5 | 45 |
| | | | | 8.0 | 63 |
| | | | | 8.5 | 66 |
| | | 25 | 10 | 7.5 | 31 |
| | | | | 8.0 | 49 |
| | | | | 8.5 | 61 |
| | | | 30 | 7.5 | 31 |
| | | | | 8.0 | 49 |
| | | | | 8.5 | 62 |

Results:

It was observed that when Trypsin and Carboxypeptidase were added together in the reaction mixture, both Des octapeptide form and des-threonine formation was not observed. At the end of the reaction Aspart is the main product in the reaction. The purity and the yield of the generated Aspart vary in individual reaction condition. The best yield of 75% of Aspart was observed under Trypsin concentration of 50 mg/L, Carboxypeptidase concentration of 10 mg/L and at pH 8.5.

Example 4B (II)

5 gm of Lispro precursor crystal was dissolved in 25 ml of 1M TRIS solution. Product concentration of the solution was maintained to 5 mg/ml and TRIS concentration was maintained to 0.6 M by adding. Aliquots of certain amounts were taken by adjusting the pH of the reaction mixture by 2.5N NaOH or 2N Glacial acetic acid. Aliquots of the reaction mixture at pH 7.0, 7.5, 8.0, 8.5, 9.0 were prepared. 1 ml each of this reaction mixture was taken into each tube and labeled as sample A, B, C etc. The reaction was carried out in all the samples by adding trypsin and Carboxypeptidase B together at different concentrations. The different conditions are tabulated.

Constant Parameters:
Product concentration 5 g/L
TRIS buffer concentration 0.6 M
Varied Parameters:
Trypsin concentration: 25-200 mg/L
Carboxypeptidase concentration: 10-30 mg/L
pH: 7.0-9.0.

| Precursor concentration (g/L) | Tris concentration (M) | Trypsin concentration mg/L | Carboxypeptidase B concentration (mg/L) | pH | Yield (%) |
|---|---|---|---|---|---|
| 5 | 0.6 | 200 | 10 | 7.0 | 33 |
| | | | | 7.5 | 49 |
| | | | | 8.0 | 62 |
| | | | | 8.5 | 65 |
| | | | | 9.0 | 29 |
| | | | 30 | 7.0 | 52 |
| | | | | 7.5 | 55 |
| | | | | 8.0 | 61 |
| | | | | 8.5 | 64 |
| | | | | 9.0 | 26 |
| | | 100 | 10 | 7.0 | 11 |
| | | | | 7.5 | 34 |
| | | | | 8.0 | 55 |
| | | | | 8.5 | 59 |
| | | | | 9.0 | 31 |
| | | | 30 | 7.0 | 24 |
| | | | | 7.5 | 41 |
| | | | | 8.0 | 54 |
| | | | | 8.5 | 66 |
| | | | | 9.0 | 34 |
| | | 50 | 10 | 7.0 | 21 |
| | | | | 7.5 | 46 |
| | | | | 8.0 | 66 |
| | | | | 8.5 | 78 |
| | | | | 9.0 | 62 |
| | | | 30 | 7.0 | 38 |
| | | | | 7.5 | 55 |
| | | | | 8.0 | 64 |
| | | | | 8.5 | 71 |
| | | | | 9.0 | 65 |
| | | 25 | 10 | 7.0 | 13 |
| | | | | 7.5 | 25 |
| | | | | 8.0 | 41 |
| | | | | 8.5 | 44 |
| | | | | 9.0 | 51 |
| | | | 30 | 7.0 | 22 |
| | | | | 7.5 | 25 |
| | | | | 8.0 | 33 |
| | | | | 8.5 | 46 |
| | | | | 9.0 | 55 |

Results:

It was observed that when Trypsin and Carboxypeptidase were added together in the reaction mixture, both Des octapeptide form and des-threonine formation was not observed. The best yield of 78% of Lispro was observed under Trypsin concentration of 50 mg/L, Carboxypeptidase concentration of 10 mg/L and at pH 8.5

Example 4B (III)

5 gm of Glulisine precursor crystal was dissolved in 25 ml of 1M TRIS solution. Product concentration of the solution was maintained to 5 mg/ml and TRIS concentration was maintained to 0.6 M by adding. Aliquots of certain amounts were taken by adjusting the pH of the reaction mixture by 2.5N NaOH or 2N Glacial acetic acid. Aliquots of the reaction mixture at pH 7.0, 7.5, 8.0, 8.5, 9.0 were prepared. 1 ml each of this reaction mixture was taken into each tube and labeled as sample A, B, C etc. The reaction was carried out in all the samples by adding trypsin and Carboxypeptidase B together at different concentrations. The different conditions are tabulated.

Constant Parameters:
Product concentration 5 g/L
TRIS buffer concentration 0.6 M
Varied Parameters:

Trypsin concentration: 25-200 mg/L
Carboxypeptidase concentration: 10-30 mg/L
pH: 7.0-9.0.

| Precursor concentration (g/L) | Tris concentration (M) | Trypsin concentration mg/L | Carboxypeptidase B concentration (mg/L) | pH | Yield (%) |
|---|---|---|---|---|---|
| 5 | 0.6 | 200 | 10 | 7.0 | 29 |
| | | | | 7.5 | 56 |
| | | | | 8.0 | 49 |
| | | | | 8.5 | 61 |
| | | | | 9.0 | 49 |
| | | | 30 | 7.0 | 44 |
| | | | | 7.5 | 59 |
| | | | | 8.0 | 42 |
| | | | | 8.5 | 29 |
| | | | | 9.0 | 21 |
| | | 100 | 10 | 7.0 | 25 |
| | | | | 7.5 | 33 |
| | | | | 8.0 | 47 |
| | | | | 8.5 | 61 |
| | | | | 9.0 | 64 |
| | | | 30 | 7.0 | 41 |
| | | | | 7.5 | 62 |
| | | | | 8.0 | 65 |
| | | | | 8.5 | 71 |
| | | | | 9.0 | 49 |
| | | 50 | 10 | 7.0 | 28 |
| | | | | 7.5 | 46 |
| | | | | 8.0 | 68 |
| | | | | 8.5 | 78 |
| | | | | 9.0 | 70 |
| | | | 30 | 7.0 | 36 |
| | | | | 7.5 | 44 |
| | | | | 8.0 | 59 |
| | | | | 8.5 | 69 |
| | | | | 9.0 | 72 |
| | | 25 | 10 | 7.0 | 14 |
| | | | | 7.5 | 29 |
| | | | | 8.0 | 35 |
| | | | | 8.5 | 49 |
| | | | | 9.0 | 51 |
| | | | 30 | 7.0 | 24 |
| | | | | 7.5 | 35 |
| | | | | 8.0 | 44 |
| | | | | 8.5 | 64 |
| | | | | 9.0 | 68 |

Results: The best yield of 78% of Glulisine was observed under Trypsin concentration of 50 mg/L, Carboxypeptidase concentration of 10 mg/L and at pH 8.5.

Example 5

Final Precipitation

The best conditions explained above for the enzyme reactions for corresponding precursor of Lispro, Aspart and Glulisine were performed.

The Individual end enzyme reaction mixture was precipitated by adding citric acid buffer and $ZnCl_2$ solution, and adjusting the pH. (The citric acid buffer comprises 15.4 g/L citric acid (anhydrous), 90 g/L di-sodium orthophosphate (anhydrous) buffer, pH adjusted to 6.3.+0.1, with o-phosphoric acid). The precipitation was done at a pH range of 4.0 to 10.0, preferably 6.0 to 8.0. The product concentration was preferably 1-10 g/L. After the precipitation, the product was separated from the clear supernatant by either centrifuging or decanting the supernatant without disturbing the settled precipitate. The precipitate so obtained was washed with chilled water to remove the unbound ions present.

The yield of the precipitation process is 85-90%.

The above description and examples have been given for ease of understanding only. No unnecessary limitations should be understood therefrom, as modifications will be obvious to those skilled in the art who will recognize that the invention can be practiced with modifications and variations within the spirit of the appended claims.

The instrumentalities reported herein overcome the problems that are outlined above and advance the art by providing a reaction method that inhibits loss of product and has ease of operation relative to other known methods. This system reduces costs by using described methodologies to achieve a given enhanced conversion efficiency relative to any known process, thus overcoming major disadvantages known in this domain of art.

We claim:

1. A process for converting insulin aspart, insulin lispro, and insulin glulisine from their corresponding insulin precursors represented by the formula:

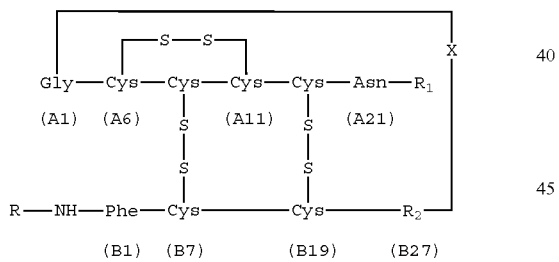

where,

R is hydrogen or a chemically or enzymatically cleavable amino acid residue or a chemically or enzymatically cleavable peptide comprising at least two amino acid residues;

$R_1$ is OH or an amino acid residue, or $Y_1$-$Y_2$ in which Y is an amino acid residue;

the moieties A1 to A21 corresponds to insulin A chain and the moieties B1 to B27 corresponds to insulin B chain including amino acid substitution, deletion and/or additions thereof;

$R_2$ is $Z_1$-$Z_2$ wherein $Z_1$ is selected from Pro, Lys, Asp and $Z_2$ is selected from Lys or Pro or Glu or $Z_1$-$Z_2$-$Z_3$ wherein $Z_1$ is selected from Pro, Lys, Asp and $Z_2$ is selected from Lys or Pro or Glu and $Z_3$ is threonine or a peptide moiety of at least three amino acid residues with the provision that the amino acid corresponding to B30 is threonine;

X is a polypeptide that connects the A chain to the B chain which can be cleaved enzymatically without disrupting either the A chain or the B chain bearing at least two amino acids wherein the first and the last amino acid is Lysine or Arginine, said precursor defined by an amino acid sequence which is at least 95% homologous to the amino acid sequence as set forth in SEQ IDs 1, 2, or 3, wherein A and B chains of such precursor are identical to A and B chains of aspart; or said precursor defined by an amino acid sequence which is at least 95% homologous to the amino acid sequence as set forth in SEQ IDs 4, 5 or 6, wherein A and B chains of such precursor are identical to A and B chains of lispro; or said precursor defined by an amino acid sequence which is at least 95% homologous to the amino acid sequence as set forth in SEQ IDs 7, 8 or 9, wherein A and B chains of such precursor are identical to A and B chains of glulisine; and wherein the process consists of treating said precursor at pH of about 7.0 to 9.0 with trypsin and carboxypeptidase used combinatorially and concurrently provided that the relative concentration ratio of trypsin to carboxypeptidase is from 5:6 to 50:1 to yield at least 75% of aspart, lispro or glulisine respectively devoid of impurities des-octapeptide and des-threonine.

2. The process according to claim 1, wherein the relative amount of trypsin to that of the insulin precursor is about 1:100.

3. The process according to claim 1, wherein the relative amount of carboxypeptidase to that of the insulin precursor is about 1:500.

4. The process according to claim 1, wherein the concentration of trypsin used for the conversion reaction is at least 0.01 mg/ml.

5. The process according to claim 1, wherein the concentration of carboxypeptidase used for the conversion reaction is at least 0.001 mg/ml.

6. The process according to claim 1, wherein the precursor is either in liquid or crystal form.

7. The process according to claim 1, wherein the conversion reaction is carried out at a temperature ranging from about 2° C. to 40° C.

8. The process according to claim 1, wherein the duration of the enzymatic conversion reaction is about 2 to 24 hours.

9. The process according to claim 1, wherein the reaction medium contains at least 30% water or a water miscible solvent.

10. The process according to claim 9, wherein the water miscible solvent is selected from the group consisting of comprising methanol, ethanol, acetone or N,N-dimethylformamide.

11. The process according to claim 9, wherein the reaction medium further comprises a salt acting as a buffering agent.

12. The process according to claim 10, wherein the salt is selected from the group consisting of TRIS, ethylenediamine, triethanolamine, glycine, and HEPES (N-2-hydroxy-ethylpiperazine-N'-2-ethanesulfonic acid).

13. The process according to claim 11, wherein the concentration of salt used in the reaction medium is about 10 mM to 1 M.

14. The process according to claim 13, wherein the concentration of salt used in the reaction medium is about 0.6 M.

15. A process for obtaining an insulin aspart, insulin lispro and insulin glulisine thereof from their respective precursor counterparts, said precursors defined by an amino acid sequence which is at least 95% homologous to the amino acid sequence as set forth in SEQ IDs 1, 2, 3, wherein
  A and B chains of such precursor are identical to A and B chains of aspart; or
  said precursor defined by an amino acid sequence which is at least 95% homologous to the amino acid sequence as set forth in SEQ IDs 4, 5 or 6, wherein A and B chains of such precursor are identical to A and B chains of lispro; or
  said precursor defined by an amino acid sequence which is at least 95% homologous to the amino acid sequence as set forth in SEQ IDs 7, 8 or 9, wherein A and B chains of such precursor are identical to A and B chains of glulisine;
said process consisting of successively carrying out the following steps in the following sequential order:
  (a) dissolving the precursor of insulin aspart, insulin lispro and insulin glulisine in a buffer solution;
  (b) preparing various aliquots of the precursor solution at pH ranges of about 7.0 to 9.0;
  (c) introducing the enzymes trypsin and carboxypeptidase concurrently at a relative concentration ratio of 5:6 to t 50:1 to the various aliquots prepared as in Step (b) to obtain insulin product devoid of impurities des-octapeptide and des-threonine and incubating the mixture for about 4-10 hours; and
  (d) precipitating the desired insulin product by addition of citric acid buffer and $ZnCl_2$.

* * * * *